(12) United States Patent  
Candiotti

(10) Patent No.: US 8,512,314 B1  
(45) Date of Patent: Aug. 20, 2013

(54) PATIENT CONTROLLED ANALGESIA FOR PEDIATRIC PATIENTS

(76) Inventor: Keith Candiotti, Miami Beach, FL (US)

( * ) Notice: Subject to any disclaimer, the term of this patent is extended or adjusted under 35 U.S.C. 154(b) by 0 days.

(21) Appl. No.: 13/418,859

(22) Filed: Mar. 13, 2012

(51) Int. Cl.
*A61K 9/22* (2006.01)

(52) U.S. Cl.
USPC ............................................... 604/890.1

(58) Field of Classification Search
USPC .................................................. 604/67
See application file for complete search history.

(56) References Cited

U.S. PATENT DOCUMENTS

| | | | |
|---|---|---|---|
| 5,605,485 A * | 2/1997 | Spector | 446/72 |
| 5,697,363 A | 12/1997 | Hart | |
| 5,842,870 A | 12/1998 | Cramer | |
| 6,004,136 A | 12/1999 | Ehrenpreis | |
| 6,322,539 B1 | 11/2001 | Cook | |
| 6,463,928 B1 | 10/2002 | Buisson | |
| 6,857,427 B2 | 2/2005 | Ziegler et al. | |
| 7,886,738 B2 | 2/2011 | Walker | |
| 2004/0205875 A1 | 10/2004 | Byrne et al. | |
| 2005/0194400 A1 | 9/2005 | Berube et al. | |
| 2007/0272245 A1 | 11/2007 | Ripple et al. | |
| 2009/0242318 A1 | 10/2009 | Gross | |
| 2009/0250064 A1 | 10/2009 | Strawder | |

* cited by examiner

*Primary Examiner* — Jason Flick

(74) *Attorney, Agent, or Firm* — Gold & Rizvi, P.A.; Glenn E. Gold

(57) ABSTRACT

A patient controlled analgesia system for pediatric patients includes an infusion pump and a hand control having a depressible trigger. The hand control is operably connected to the infusion pump for selectively dosing a medication to be dispensed by the infusion pump. A patient interface object comprises a stuffed toy defining a rear opening and an internal void therein. A retainer is affixed within the internal void, and securely receives the hand control. An actuator is affixed within the internal void proximate to an outer surface of the stuffed toy and also proximate to the depressible trigger. The actuator is biased away from the depressible trigger and selectively movable to engage and disengage the depressible trigger by pressing an exterior of the stuffed toy.

9 Claims, 9 Drawing Sheets

PATIENT CONTROLLED ANALGESIA FOR PEDIATRIC PATIENTS

FIELD OF THE INVENTION

The present disclosure generally relates to analgesic delivery devices, and more particularly to a patient-controlled analgesic delivery device for pediatric patients.

BACKGROUND OF THE INVENTION

Various drugs have been developed over the years to aid an individual to recover from various illnesses and medical conditions. These medications are either administered by health care professionals or are self-administered by the patient according to the directions of a health care professional. Probably the most common medicinal drugs are those used to aid in pain management and take the form of individual tablets of mild analgesics such as 'low dose aspirin' to opioids administered by infusion pumps. The majority of these pain control medications are self-administered by the patient according to directions from the responsible health care professional treating the patient, especially when administered in the form of one or more tablets at designated time intervals.

For patients who have undergone major surgery, who are in end-stage cancer or experiencing other conditions where there is acute pain, the use of opioids or other high strength medications are needed to adequately manage the patient's pain. These medications can be administered by intramuscular injection. However, such administration typically requires a medical professional to accomplish the administration of the analgesic. The concept of a patient controlled analgesic demand system and self administration of opioids was first suggested in the early 1970's. The first commercially available infusion pump was developed in 1976, however, its use was limited to adults.

Patient Controlled Analgesia (PCA) is considered one of the most effective analgesic methods for relieving acute pain. The technique allows the administration of on-demand analgesics using an infusion pump that delivers controlled doses of pain medications when the patient presses a button. Different types of analgesics can be delivered using a PCA pump through variable routes of administration: Intravenous, intrathecal epidural perineural and transdermal, among others. PCA is now regularly used for adult patients to manage acute pain. Advantages of the use of PCA include the lack of waiting time for patients requiring pain medication before a caregiver can increase the dosage of medication. In this way, the patient spends less time in pain and as a corollary to this, patients tend to use less medication than in cases in which medication is given according to a set schedule.

Studies of PCA for use in treating children were begun in the 1980's, and is now considered an efficient and well tolerated technique for the management of acute postoperative pain in children. PCA is also useful in other areas of pediatric care such as pediatric oncology, burns, palliative care and acute painful conditions such as vaso-occlusive crisis of sickle cell anemia. PCA is a safe technique that allows a sustained analgesic level in the blood with the possibility of self administration of boluses if the pain increases.

Other benefits of PCA for children include increased patient and parent satisfaction compared to intramuscular injections of analgesics, since children are more likely to tolerate pain that to have another injection. Additional benefits realized by children using PCA include the opportunity to better estimate the pain occurring after physiotherapy, pain relief during mobilization or dressing changes and an improved sense of control over their illness. The safety and efficacy of PCA in children has been established and can be considered as a standard for the treatment of acute painful conditions for pediatric patients.

However, the primary contraindication for the use of PCA in the pediatric population is the inability of pediatric patients to understand the concept of PCA or how to activate the device. This contraindication requires that patients should be carefully screened to guarantee adequate patient selection. While age along should not be considered as a criteria for inclusion or exclusion, children who are five years of age or older are more likely to benefit from PCA. For the appropriate universe of selected pediatric patients, they, their parents, and their care givers must be provided with education regarding what to expect from PCA. For example, it should be explained that PCA helps controlling the pain rather than eliminating it and that the child must be the only one who activates the delivery of the analgesic.

Therefore, a device and associated system to help children understand and self-administer analgesic medication is needed.

SUMMARY OF THE INVENTION

The present disclosure is generally directed to a patient controlled analgesia system that satisfies the need for a system that is understood by a pediatric patient. The patient controlled analgesia system for pediatric patients includes an infusion pump and a hand control having a depressible trigger. The hand control is operably connected to the infusion pump for selectively dosing a medication to be dispensed by the infusion pump. A patient interface object comprises a stuffed toy defining a rear opening and an internal void therein. A retainer is affixed within the internal void, and securely receives the hand control. An actuator is affixed within the internal void proximate to an outer surface of the stuffed toy and also proximate to the depressible trigger. The actuator is biased away from the depressible trigger and selectively movable to engage and disengage the depressible trigger by pressing an exterior of the stuffed toy.

In another aspect, a patient interface object is used with a known patient controlled analgesia system having a hand control with a depressible trigger for activating the patient controlled analgesia system. The patient interface object comprises a stuffed toy defining a rear opening and an internal void therein. A retainer is affixed within the internal void for securely receiving the hand control. An actuator is affixed within the internal void proximate to an outer surface of the stuffed toy and also proximate to the retainer. The actuator is biased away from the retainer and is selectively movable to engage and disengage the depressible trigger of the hand control to be secured in the retainer.

In still another aspect, the retainer comprises a head having an outer flange and defining a central aperture therethrough. A body is affixed to the head wherein the body defines a longitudinal slot therealong separating the body into a first body half and a second body half. The body also defines an interior cavity for receiving the hand control therein. An annular rib on an interior of the first and said second body halves engages a portion of the hand control for securing the hand control within the retainer.

In yet another aspect, the actuator comprises a plate shaped to approximately conform to the outer surface of the stuffed toy. A finger extends rearwardly from the plate such that the finger is axially aligned with the hand control trigger and the central aperture of the retainer head. A compression spring bears against the actuator plate and the retainer head biasing the finger of the actuator away from the aperture and the depressible trigger such that pressure applied to an exterior of the stuffed toy proximate to the actuator causes the finger to selectively translate within the aperture and depress the trigger of the hand controller.

In a still further aspect, the stuffed toy is in the form of a stuffed animal.

In another aspect, the retainer is affixed within a muzzle of the stuffed animal and the actuator is positioned behind a nose of the stuffed toy animal such that pressing said nose causes the actuator to depresses the trigger of the hand controller secured within the retainer.

In another aspect, the retainer is affixed within a torso of the stuffed animal and the actuator is positioned behind a stomach area of the stuffed toy animal such that pressing the stomach area causes the actuator to depresses said trigger of the hand controller secured in the retainer.

In a still further aspect, the retainer further includes a brace plate affixed thereto wherein the brace plate is positioned proximate to a back of the stuffed toy animal, such that compression of the torso of the stuffed toy animal by a patient causes the actuator to depresses the trigger of the hand controller.

In yet another aspect, the stuffed toy of the patient interface object is constructed to resemble a form selected from the group consisting of an animal, a legendary creature, a cartoon character, and an inanimate object.

In another aspect, a method of providing patient controlled analgesia to a pediatric patient includes the steps of connecting a patient controlled analgesia system of a known type including an infusion pump and hand control to the intravenous line of a pediatric patient. The hand control is secured in a patient interface object of the type comprising a stuffed toy defining a rear opening and an internal void therein and having a retainer affixed within the internal void for securely receiving the hand control, and further including an actuator affixed within the internal void proximate to an outer surface of the stuffed toy and also proximate to the retainer wherein the actuator is biased away from the retainer and selectively movable to engage and disengage the depressible trigger of the hand control secured in the retainer. The pediatric patient is familiarized to correlate the pressing of area of the stuffed toy proximate to the actuator with relieving pain experienced by the pediatric patient. An Internet address is provided to the pediatric patient exclusively peculiar to the pediatric patient for instructions on use of the combined patient controlled analgesia system and the patient interface object.

In still another aspect, a unique alpha-numeric identifier is assigned to the patient interface object, the provided Internet page is logged into using the unique alpha-numeric identifier.

In yet another aspect, a picture of the stuffed toy representing the patient interface object is displayed on the Internet page. Information unique to the care of the pediatric patient is also listed, including at least medical treatment procedures, operating instructions of the patient controlled analgesia system with the patient interface object, and an explanation of how the patient should express pain with visual analog scales.

In another aspect, the stuffed toy form for the patient interface object is selected from the group of an animal, a legendary creature, a cartoon character, and an inanimate object.

These and other features, aspects, and advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
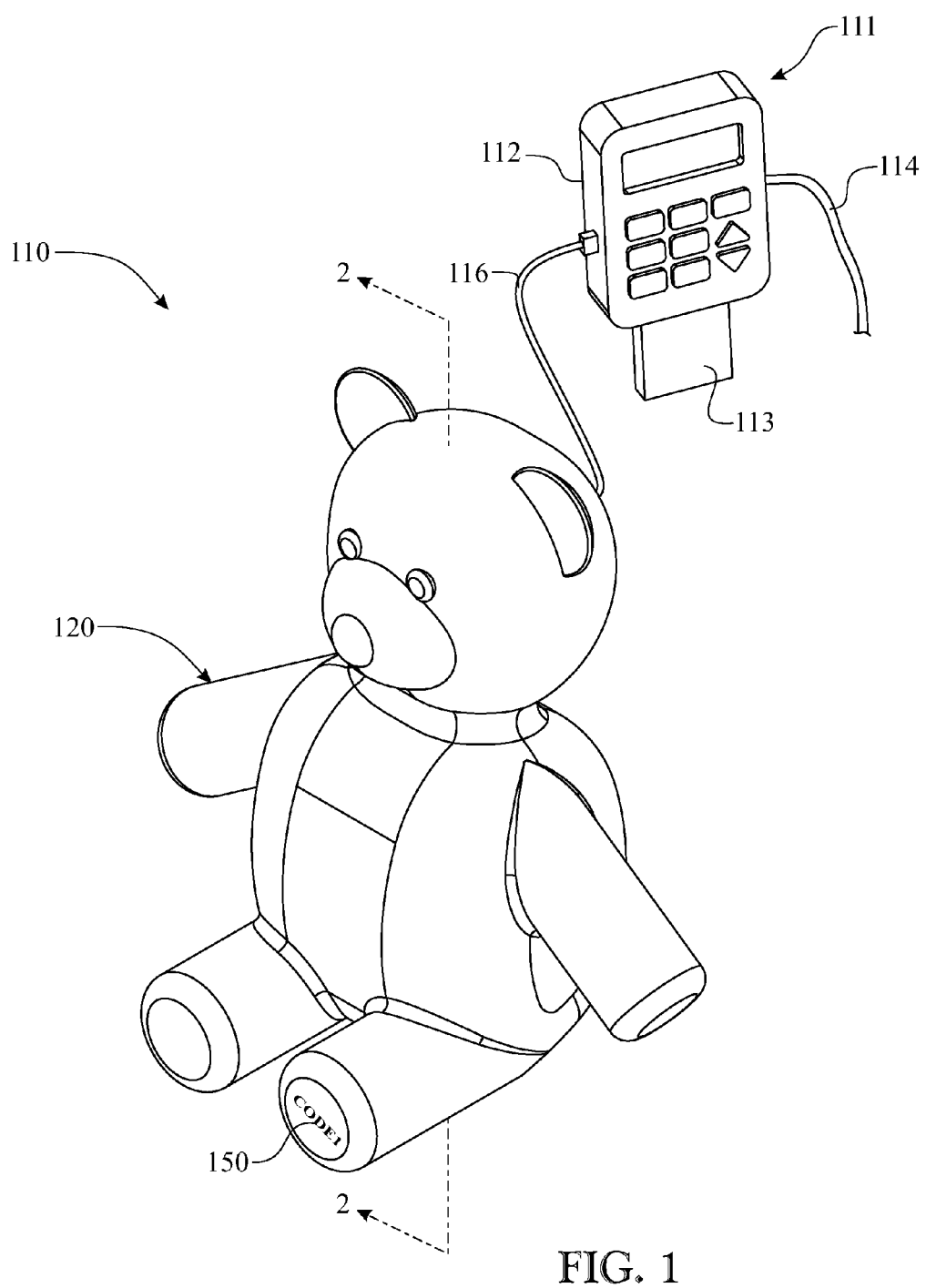
FIG. 1 presents a top isometric view of an exemplary patient controlled analgesia system for pediatric patients embodying the present invention.

Turning to the drawings, FIG. 1 shows a pediatric patient controlled analgesia (PCA) system 110 intended for use with pediatric patients which is one of the preferred embodiments of the present invention and illustrates its various components. The pediatric PCA system 110 includes a patient controlled analgesia system 111 of a known design and a patient interface object 120.

Figure 2:
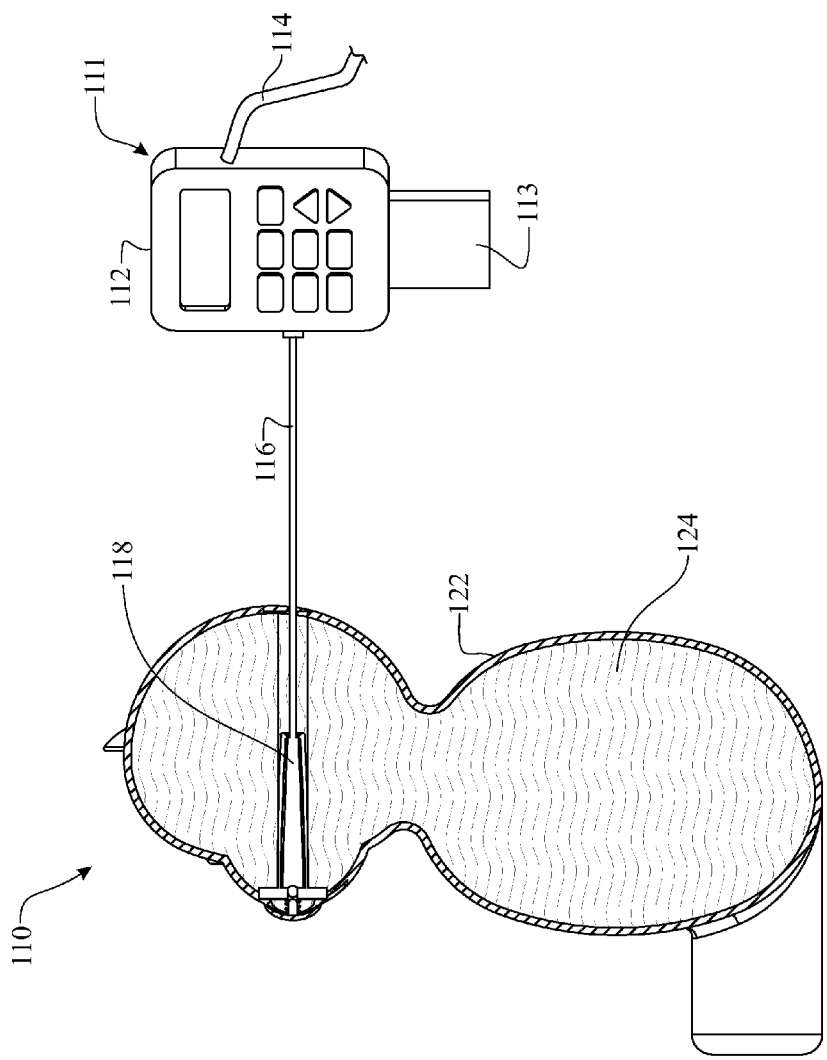
FIG. 2 presents a cross-sectional view of the patient controlled analgesia system for pediatric patients shown in FIG. 1, with the section being taken along the line 2-2 of FIG. 1.

Turning now to FIGS. 1 and 2, the patient controlled analgesia system 111 includes an infusion pump 112 for controlling and delivering an analgesic drawn from an analgesic reservoir 113 to a patient through an intravenous line 114. The infusion pump 112 can be individually programmed to deliver a predetermined quantity of analgesic at the administration of each of patient demanded periodic doses. The infusion pump 112 also limits the number of doses over a set time period as determined by an attending health professional to prevent overdosing. The patient controlled analgesia system 111 also includes a hand control 118 operatively connected to infusion pump 112 by a cable 116. In this manner, the infusion pump 112 can typically be affixed to a stand proximate to the patient and the dispensing trigger can be held by or within reach of the patient.

The patient interface object 120, as illustrated in FIGS. 1 and 2, is a stuffed or plush toy in the form commonly known as a "teddy bear." It is well understood that other forms are contemplated and the exemplary "teddy bear" form illustrated herein is meant to be representative and not limited to that of the illustrated teddy bear and can be made in many different forms to resemble animals, legendary creatures, cartoon characters or inanimate objects. The patient interface object 120 has a fabric exterior 122 and is sewn from multiple panels of cloth, plush, or other textiles to form the desired shape. The fabric exterior defines an interior that is filled with a stuffing 124 such as, but not limited to, excelsior, beans, plastic pellets, cotton, synthetic fibers, or other similar materials to provide substance to patient interface object 120 and which are known in the plush toy industry.

Figure 3:
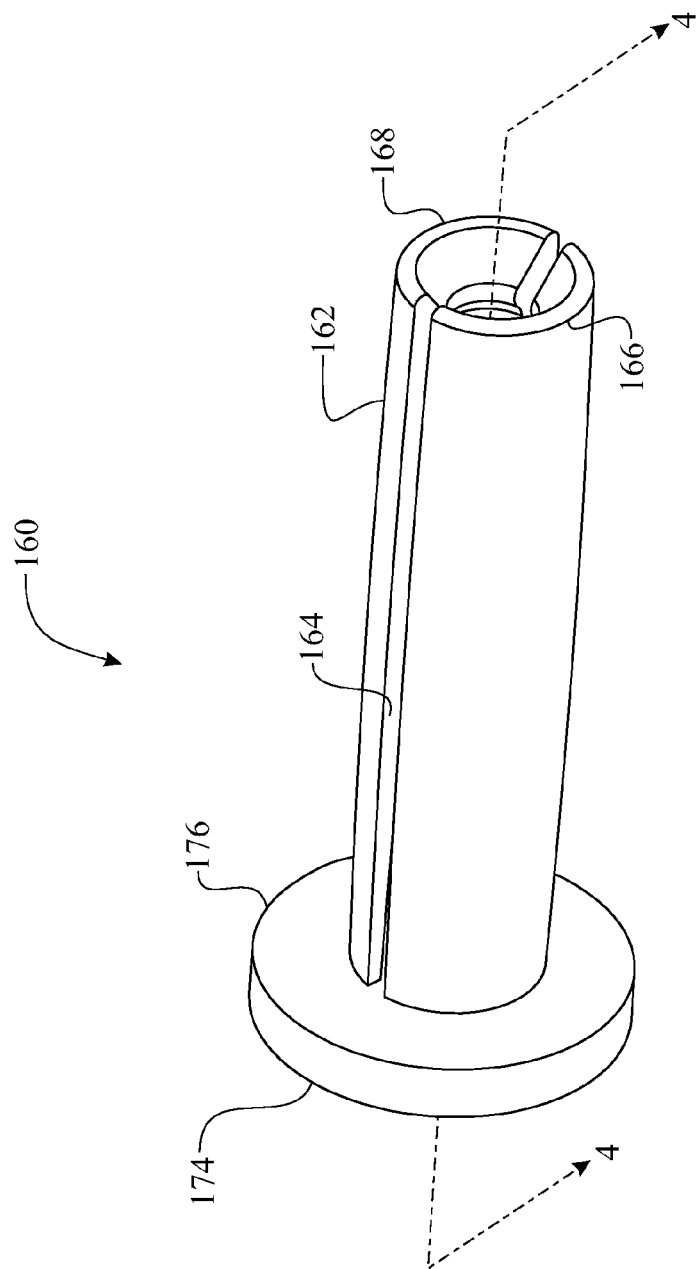
FIG. 3 presents a top isometric view of a dispensing trigger retainer.
Figure 4:
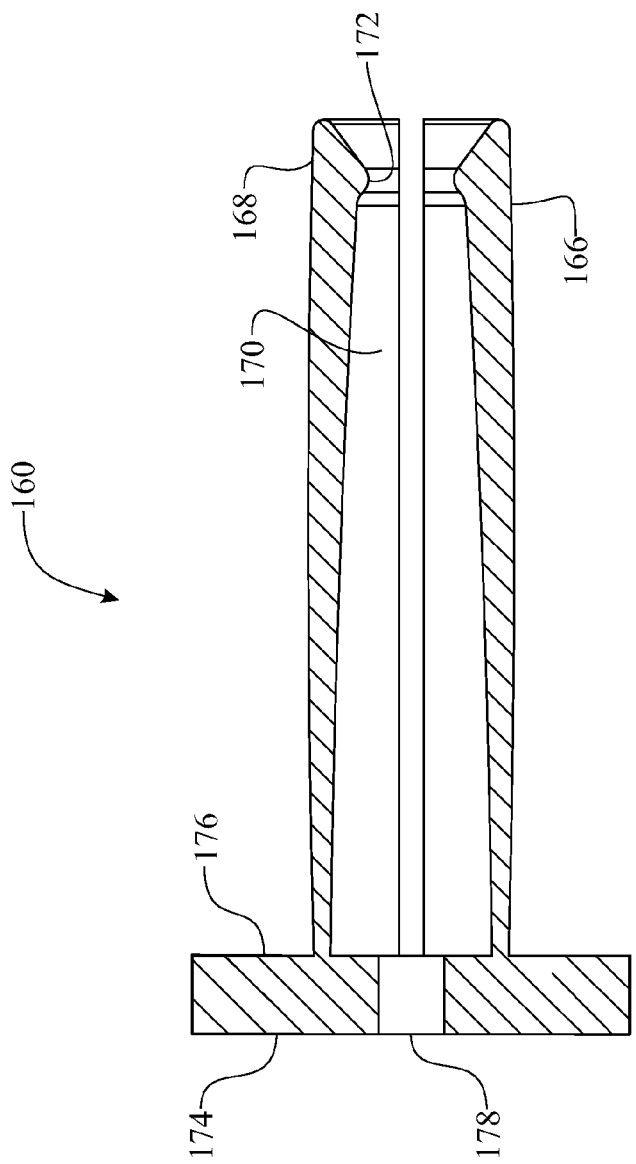
FIG. 4 presents a cross-sectional view of the dispensing trigger retainer shown in FIG. 3, with the section being taken along the line 4-4 of FIG. 3.
Figure 5:
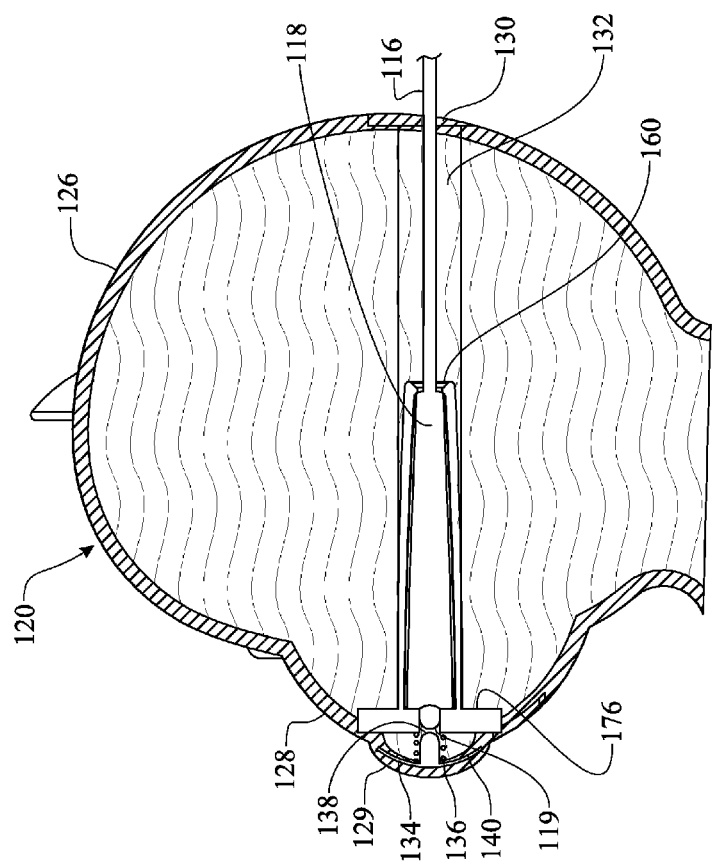
FIG. 5 presents an enlarged cross-sectional view of the portion of the patient interface receiving the dispensing trigger illustrating the dispensing trigger in an unactivated condition.

As shown in FIGS. 2 and 5, the patient interface object 120 defines an opening 130 at the rear of the bear's head 126. The opening 130 permits access to an interior void 132 in which is positioned a retainer 160. The retainer 160 is most clearly illustrated in FIGS. 3 and 4 wherein the retainer 160 has a flat washer like head 174 having a flange 176 and defining a central aperture 178 therethrough. It is understood that the flange 176 can be shaped to contour to a mating section of the patient interface object 122. A cylindrical body 162 extends rearwardly from head 174. A longitudinal slot 164 divides the cylindrical body 162 into a first body half 166 and a second body half 168. The body halves 166 and 168 further define an internal cavity 170 which is shaped to receive the hand control 118 in a manner such that the trigger button 119 is substantially in registration with the central aperture 178. The body halves 166 and 168 further include an internal annular rib 172 positioned to engage with a portion of hand control 118 to securely retain the hand control 118 within the retainer 160. The slot 164 permits the body halves 166 and 168 to radially separate one from the other at an end opposite from the head 174 such that the hand control 118 can be axially inserted to and translated along the length of the retainer 160 until fully engaged in cavity 170. The resiliency of body halves cause them to closely engage about the exterior of the hand control 118 and further that the annular rib 172 engages with a rear portion of the hand control 118 to securely retain the hand control 118 therein.

As most clearly illustrated in FIG. 5, the retainer 160 is positioned within the interior void 132, proximate to the front of the bear's head 126, and particularly, in alignment with the bear's muzzle 128. The flange 176 of the retainer 160 is secured to the fabric exterior 122 of the bear's muzzle 128 by gluing, sewing, riveting, or other known methods of securing. An actuator 134 is interposed between the bear's nose 129 and the flange 176. The actuator 134 comprises a plate 140 which can be flat or shaped to approximate the contour of the area of the patient interface object 120 proximate to the actuator 134. A finger 138 of a diameter smaller than central aperture 178 extends rearwardly from the plate 140 and is axially aligned with the aperture 178. A compression spring 136 is interposed between the plate 140 and the head 174 to bias the actuator 134 away from the retainer 160.

In use, and referring to FIGS. 1 through 6, when a patient controlled analgesia system 111 is desired to be used for a pediatric patient, the patient controlled analgesia system 111 has a bolus or reservoir of medication 113 coupled with the infusion pump 112 in a known manner as well as connecting the delivery line 114 into a previously established patient's intravenous line. A patient interface object 120, such as the illustrated exemplary teddy bear, is selected that is pleasing and comforting to the pediatric patient, possibly even selected by the pediatric patient.

The hand control 118 is inserted through the opening 130 provided in the back of the bear's head 126 and longitudinally inserted into the cavity 170 of the retainer 160, until trigger button is engage in the central aperture 178 and the annular rib 172 engages the rear of the hand control 118, thus securing the hand control 118 within the retainer 160. Once the medical professional in attendance for the pediatric has programmed the infusion pump 112 for individual dosage quantities, and maximum dosage over a set period of time, the pediatric patient controlled analgesia system 110 is ready for use.

Figure 6:
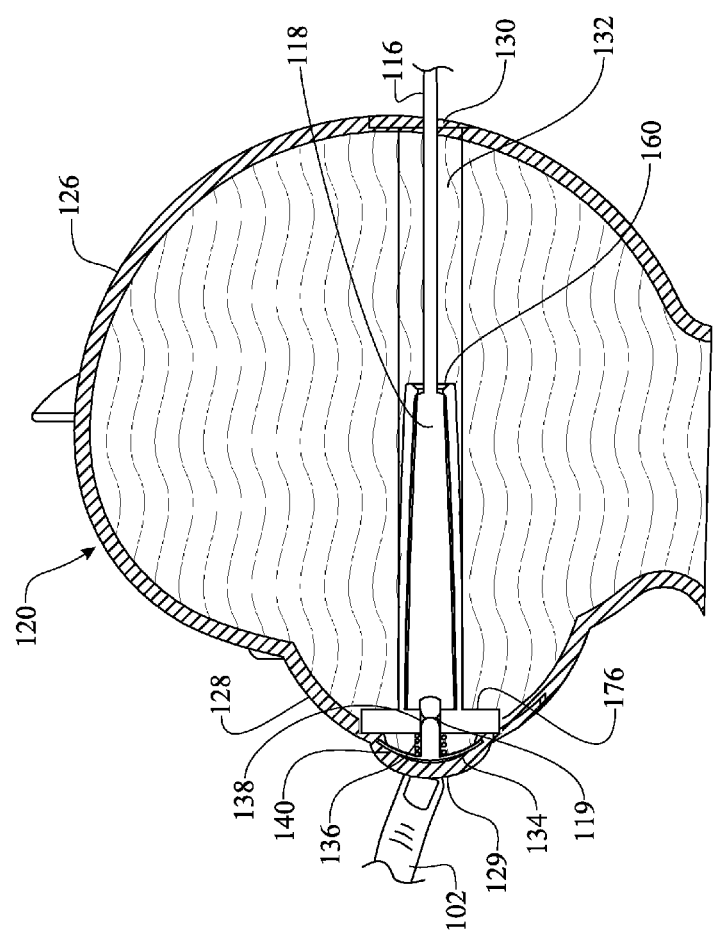
FIG. 6 presents an enlarged cross-sectional view of the portion of the patient interface receiving the dispensing trigger illustrating the dispensing trigger in an activated condition.

The cable 116 permits the infusion pump 112 to be mounted to a stand close by, but not requiring to be on the patient's bed. The patient interface object 120 having the hand control 118 secured therein can then be given to the pediatric patient. When the system 110 is in an unactivated state where no medication from reservoir 113 is being administered to the pediatric patient, the finger 138 of the actuator 134 is biased away from trigger button 119 by biasing spring 136. Referring now to FIG. 6, when the pediatric patient is experiencing pain and desires relief from the pain, the patient can us a thumb 102 (or other finger) to press the bear's nose 129. Because of the proximity of the plate 140 of the actuator 134 to the bear's nose 129, as the nose 129 is depressed, the actuator 134 is similarly depressed overcoming the biasing force of the spring 136. Since the flange 176 is affixed to the bear's muzzle 128 and is substantially immovable with respect to the bear's nose 129, the finger 138 of the actuator 134 translates through the aperture 178 of the retainer 160 and engages with the trigger button 119 of the hand control 118. With sufficient axial travel of the finger 138, the trigger button 119 is depressed sending a signal to the infusion pump 112 to dispense a predetermined dosage of medicine from the reservoir 113 in accordance with the preprogrammed guidelines established by the attending health professional. Once the desired dosage has been administered, the system 110 again reverts to an "at rest" status according to FIG. 5 until such time as the pediatric patient desires another dosage of medicine dispensed.

Figure 9:
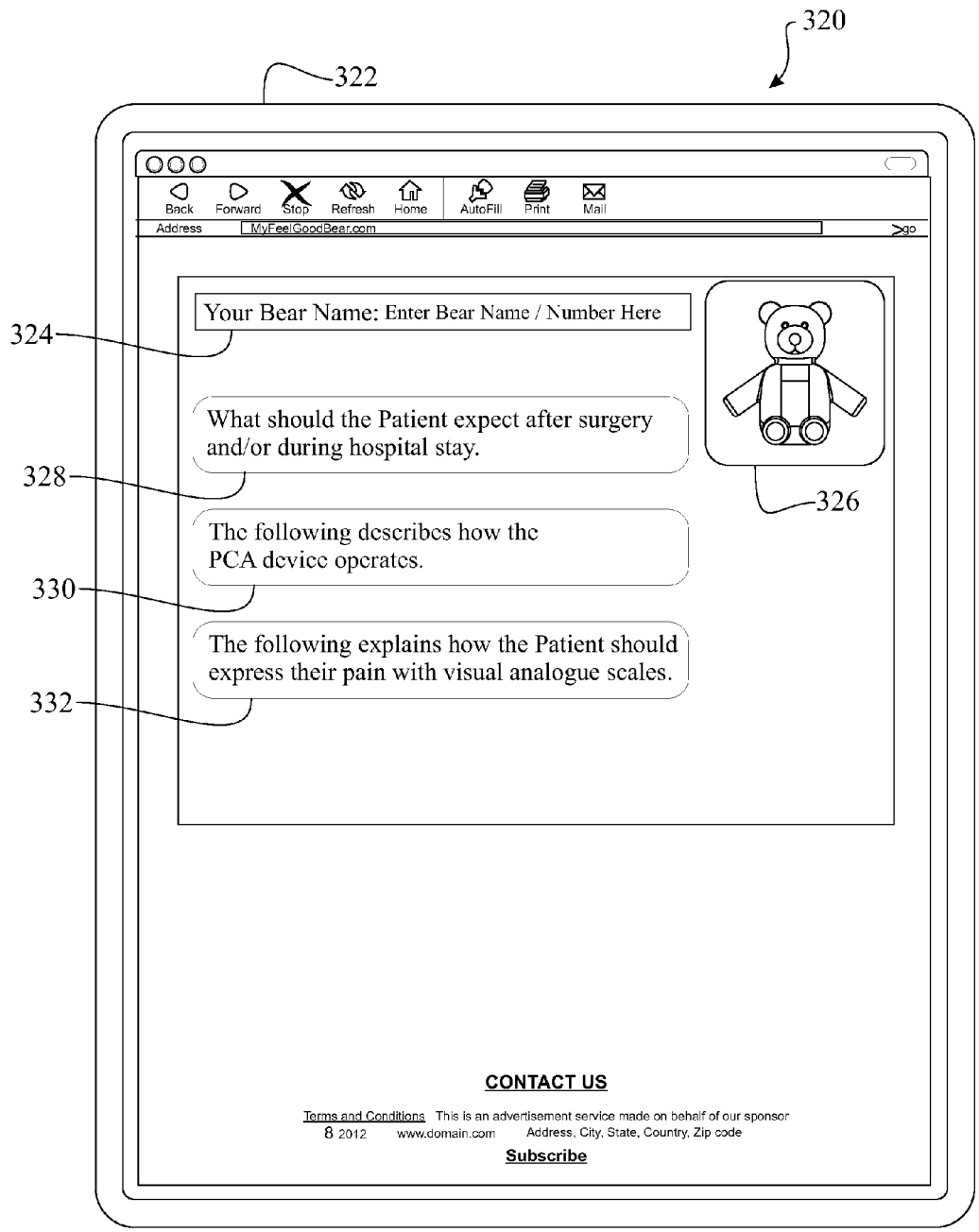
FIG. 9 presents a representative Internet web page providing interaction instructions for the patient controlled analgesia system.

Referring now to FIG. 9, a pediatric patient and his or her parents can be familiarized to the system 110 and receive introduction to the usage and operating directions for system 110 via an Internet connection. FIG. 9 illustrates a representative web page 320 for introduction and use of system 110. Upon receiving an Internet web address from the attending medical professional and seeing the web page 320 displayed, the user logs into the page by entering a unique alpha-numeric identifier 150 into a login field 324. The alpha-numeric identifier 150 is unique to the selected patient interface object 120, such that when the alpha-numeric identifier 150 is entered into the login field 324, a picture 326 of the patient's personal interface object 120 is displayed further personalizing the Internet web page. Also contained on the web page 320 or following pages, the pediatric patient can receive additional information such as an entertaining story about the object 120, an area 328 describing what the patient's hospital stay will entail and what the patient can expect to experience at different stages such as prior to and subsequent to surgery. A second area 330 can describe how the patient controlled analgesia system 110 operates, and a third page area 332 can explain how the pediatric patient should express their pain by relating to visual associations, depictions, or scales. Other information of interest, either general or patient specific, can also be presented to the patient on the displayed web page, since the page is unique and dedicated to the patient associated with the patient interface object 120 represented by the alpha-numeric code 150 used in the login process. It is understood that the information can be provided in a single web page as illustrated or separated into multiple web pages for ease of use.

Figure 7:
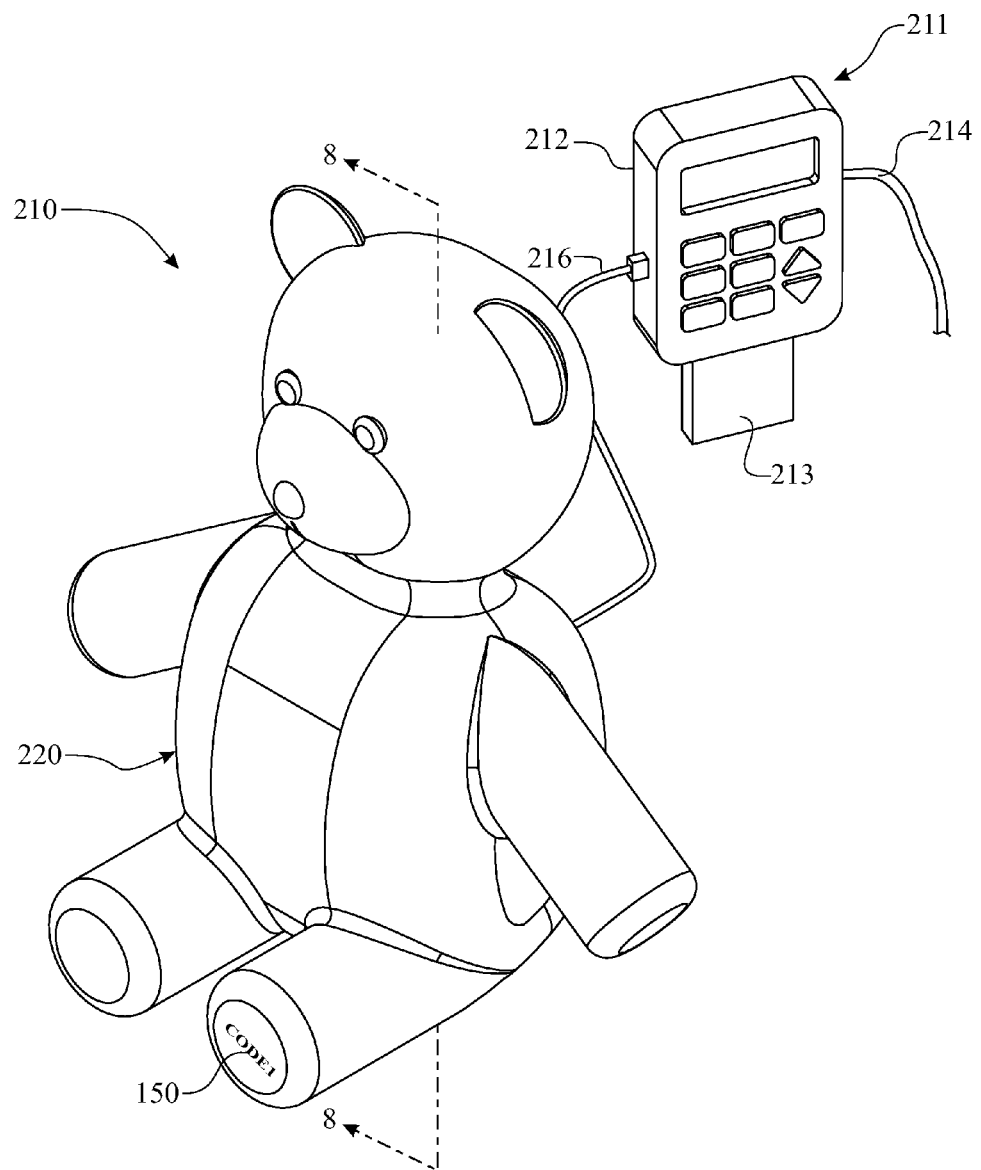
FIG. 7 presents a top isometric view of an alternate exemplary embodiment patient controlled analgesia system for pediatric patients.
Figure 8:
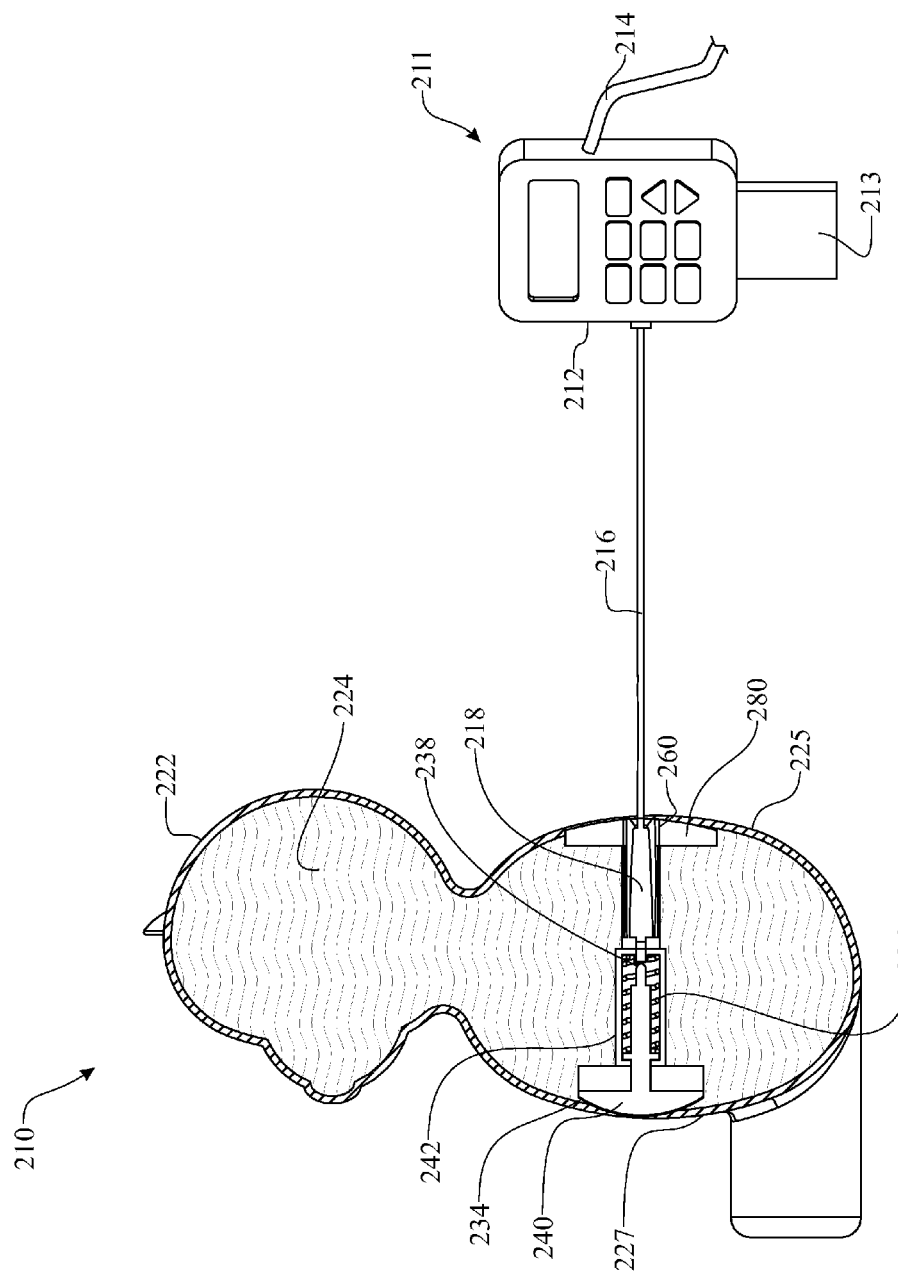
FIG. 8 presents a cross-sectional view of the patient controlled analgesia system for pediatric patients shown in FIG. 7, with the section being taken along the line 8—8 of FIG. 7.

An alternate embodiment pediatric patient controlled analgesia system 210 is illustrated in FIGS. 7 and 8. While not every feature identified by a reference number in FIGS. 7 and 8 may be discussed herein, like features of system 210 with respect to features of system 110 as described above have similar reference numbers preceded by the numeral "2" in lieu of the numeral "1". The alternate embodiment pediatric patient controlled analgesia system 210 differs from system 110 in that the hand control 218 is located in the bear's abdomen 227. The retainer 260 again is formed to receive and secure the hand control 218, however the retainer 260 also includes a brace plate 280 positioned proximate to the bear's back 225. The actuator 234 includes a plate 240 positioned proximate to the front abdomen area 227 of the bear 222. A biasing unit 242, including a biasing spring 236, is interposed between the actuator 234 and the receiver 260. The biasing unit 242 biases the plate 240 toward the bear's abdomen 227.

In use, a pediatric patient experiencing pain and wishing relief from the pain can initiate dispensing of medicine from the reservoir 213 by the infusion pump 212 by hugging the patient interface object 220. The force of the patient's hug about the torso area causes the bear's abdomen 227 to be compressed toward the bear's back 225. This compression, in turn, causes the plate 240 of the actuator 234 to be compressed toward the brace plate 280 thereby causing the finger 238 to longitudinally translate with respect to the patient control 218 and engaging the trigger button of the patient control 218. When the trigger button of the patient control 218 is eventually depressed upon full travel of the finger 238 a dispensing signal is transmitted to the infusion pump 212 and medicine is dispensed from the reservoir 213 through the intravenous line 214 to the patient.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A patient controlled analgesia system for pediatric patients, said patient controlled analgesia system comprising:
   a medical infusion pump in fluid communication with an intravenous line, wherein the intravenous line is connected to the patient;
   a hand control having a depressible trigger, said hand control operably connected to said infusion pump for selectively dosing and subsequently dispensing a medication by said infusion pump to said pediatric patient via said intravenous line;
   a patient interface object comprising:
      a children's toy comprising an internal void therein accessible via an opening through an exterior portion of said children's toy;
      a retainer affixed within said internal void, said retainer securely receiving said hand control; and
      an actuator affixed within said internal void proximate to an outer surface of said children's toy and also proximate to said depressible trigger, said actuator biased away from said depressible trigger and said actuator selectively movable to engage and disengage said depressible trigger.

2. A patient controlled analgesia system for pediatric patients according to claim 1 wherein said retainer comprises:
   a head having an outer flange and defining a central aperture therethrough;
   a body affixed to said head, said body defining a longitudinal slot therealong separating said body into a first body half and a second body half, and further defining an interior cavity receiving said hand control therein; and
   an annular rib on an interior of said first and said second body halves engaging a portion of said hand control for securing said hand control within said retainer.

3. A patient controlled analgesia system for pediatric patients according to claim 2 wherein said actuator comprises:
   a plate shaped to approximately conform to said outer surface of said children's toy;
   a finger extending rearwardly from said plate, said finger axially aligned with said hand control trigger and said central aperture of said retainer head; and
   a compression spring bearing against said actuator plate and said retainer head, said compression spring biasing said finger of said actuator away from said depressible trigger such that pressure applied to an exterior of said children's toy proximate to said actuator causes said finger to selectively depress said trigger of said hand controller.

4. A patient controlled analgesia system for pediatric patients according to claim 3 wherein said children's toy is in the form of a stuffed animal.

5. A patient controlled analgesia system pediatric patients according to claim 4 wherein said retainer is affixed within a muzzle of said stuffed animal and said actuator is positioned behind a nose of said stuffed toy animal such that pressing said nose causes said actuator to depresses said trigger of said hand controller.

6. A patient controlled analgesia system for pediatric patients according to claim 4 wherein said retainer is affixed within a torso of said stuffed animal and said actuator is positioned behind a stomach area of said stuffed toy animal such that pressing said stomach area causes said actuator to depresses said trigger of said hand controller.

7. A patient controlled analgesia system for pediatric patients according to claim 6 wherein said retainer further includes a brace plate affixed thereto and positioned proximate to a back of said stuffed toy animal, such that compression of said torso of said stuffed toy animal by a patient causes said actuator to depresses said trigger of said hand controller.

8. A patient controlled analgesia system for pediatric patients according to claim 1 wherein said children's toy of said patient interface object is constructed to resemble a form selected from the group consisting of an animal, a legendary creature, and a cartoon character.

9. A patient controlled analgesia system for pediatric patients according to claim 6 wherein said retainer further includes a brace plate affixed thereto and positioned proximate to a back of said stuffed toy animal, such that compression of said torso of said stuffed toy animal by said pediatric patient causes said finger of said actuator to selectively translate within said aperture in said retainer head.

* * * * *